United States Patent
Patashnick et al.

[11] Patent Number: 6,151,953
[45] Date of Patent: Nov. 28, 2000

[54] GAS STREAM CONDITIONING APPARATUS, SYSTEM AND METHOD FOR USE IN MEASURING PARTICULATE MATTER

[75] Inventors: Harvey Patashnick, Voorheesville; John Hiss, III, Castleton, both of N.Y.

[73] Assignee: Rupprecht & Patashnick Company, Inc., Albany, N.Y.

[21] Appl. No.: 09/014,252

[22] Filed: Jan. 27, 1998

[51] Int. Cl.[7] .................................................. G01N 1/00
[52] U.S. Cl. ........................................................ 73/28.01
[58] Field of Search ........................... 73/28.01, 863.01, 73/863.11, 863.12, 863.21, 863.23, 863.22, 864.81; 165/222, 223, 224, 229, 253, 281, 291

[56] References Cited

U.S. PATENT DOCUMENTS

| | | | |
|---|---|---|---|
| 4,449,816 | 5/1984 | Kohska et al. | 73/28.01 |
| 4,710,887 | 12/1987 | Ho | 364/555 |
| 4,764,758 | 8/1988 | Skala | 73/865.5 |
| 4,852,389 | 8/1989 | Mayer et al. | 73/38 |
| 5,090,233 | 2/1992 | Kogure et al. | 73/28.05 |
| 5,107,696 | 4/1992 | Mayer et al. | 73/38 |
| 5,410,401 | 4/1995 | Shofner et al. | 356/238 |
| 5,553,507 | 9/1996 | Basch et al. | 73/863.01 |
| 5,571,945 | 11/1996 | Koutrakis et al. | 73/28.03 |
| 5,665,902 | 9/1997 | Wang et al. | 73/864.81 |

OTHER PUBLICATIONS

TEOM Series 1400A Ambient Particulate Monitor—Automated Particulate Mass Measurement brochure, Mar. 1993.

*Primary Examiner*—Robert Raevis
*Attorney, Agent, or Firm*—Heslin & Rothenberg, P.C.

[57] ABSTRACT

A conditioner, system and methods for conditioning a sample gas stream for particulate matter measurement purposes employs a sample gas stream conduit having an inlet and an outlet and a sample gas stream conditioner in communication with the sample gas stream conduit. The sample gas stream conditioner includes a moisture control system, wherein the moisture control system regulates a humidity level of the sample gas stream flowing through the sample gas stream conduit to maintain a selectable humidity level at the particulate matter collector. A particulate matter measurement instrument is in communication with the sample gas stream outlet and measures the particulate matter in the sample gas stream. Alternative methods for regulating the humidity level at a particulate matter collector in the measurement instrument are also disclosed.

47 Claims, 2 Drawing Sheets

GAS STREAM CONDITIONING APPARATUS, SYSTEM AND METHOD FOR USE IN MEASURING PARTICULATE MATTER

FIELD OF THE INVENTION

This invention generally relates to the measurement of particulate matter suspended in a gaseous fluid medium, such as particulate matter suspended in ambient air. More particularly, this invention concerns an apparatus and method for controlling the thermodynamic conditions of a sample gas stream in order to more accurately measure suspended particulate matter in the gas stream, preferably under near real-time conditions.

BACKGROUND OF THE INVENTION

The measurement of particulate matter in ambient air is important for a variety of reasons, the most important of which is related to health effects. Suspended particulate matter is known to produce a variety of deleterious health effects when inhaled. As a result, regulatory agencies around the world require monitoring of the levels of particulate matter. The levels are measured in terms of concentration, i.e., micrograms of particulate matter per cubic meter of air. Reference techniques for this measurement are presently defined in terms of a mass measurement utilizing a filter medium to capture the particulate matter and the total volume of air which has been filtered by the medium over a given period of time. There are various means available to unambiguously determine the flow rate through the filter over time (and hence the volume of the air sampled), but surprising, the mass measurement is not straightforward due to the complex nature of ambient particulate matter which results in unstable mass deposition on the filter.

Both direct and indirect measurement techniques have been employed in an effort to quantify particulate matter mass. Each method which has been developed to date, however, has limitations in obtaining a measurement of the actual mass of particulate matter as it exists in its suspended form in ambient air. Direct mass measurements as represented by weighing material captured on a substrate such as a filter media are susceptible to volatile losses which are not easily quantifiable. Indirect methods such as light scattering measurements, on the other hand, are inherently inaccurate as there is no physical connection between other properties of particles and particle mass.

As a result of these difficulties, the current reference method in the United States is a manual method dependent technique which does not necessarily provide a completely accurate measure of particulate matter as it actually exists in its undisturbed state in the air. The manual reference method consists of: (1) filter equilibration under a pre-defined range of temperature and humidity conditions (i.e., currently 20° C. to 23° C. ±2° C. and 30% to 40% ±5% relative humidity for PM-2.5 standard and 15° C. to 30° C. ±3° C. and 20% to 45% ±5% for PM-10 standard); (2) a pre-collection weighing of the filter; (3) the installation of the filter in a manual sampler and the sampling of ambient air (for a 24-hour period); (4) the removal of the filter from the sampler and a post-collection conditioning under the same equilibration conditions for the filter as performed pre-sampling; and finally, (5) post-collection weighing of the filter to determine the mass captured on the filter media.

While sampling, the manual reference method does not consider the sample gas stream or ambient air temperature or humidity conditions. In effect, this method uses only the pre-defined sampling temperature and humidity conditions before and after sampling. This method does not compensate for condition changes during sampling. While this methodology is intended to provide a consistent basis for the generation of standardized 24-hour sampling results, unfortunately it does not. First, it may give an inaccurate measurement due to failure to consider sample gas stream conditions. And second, it presents difficulties when other measurement techniques utilized in automated, near real-time samplers, for example, are compared to it.

Automated samplers have significant advantages over manual reference method samplers in that they can provide near real-time measurements at great labor cost savings (i.e., the post-collection measuring and calculating steps in the manual method are eliminated because measuring and calculating are conducted in real-time by the automated sampler). Examples of such automated samplers include inertial mass measurement ambient particle monitors and beta attenuation monitors. Further, due to their near real-time measurements of mass, these samplers respond to volatile components in ways which are not directly comparable to the reference manual method.

However, like the manual reference apparatus and method, existing automated samplers may not fully consider the temperature and humidity conditions of the sample gas during sampling while making their real-time measurements. Also, the integrated 24-hour results from the automated samplers may not always agree closely with the 24-hour single measurement from the manual reference method. Thus, although the automated samplers provide a more real-time measure of particulate matter present in a sample gas stream, they still have drawbacks, including their potential inability to absolutely conform to the manual reference method all the time.

Accordingly, a method and apparatus is needed to mitigate any differences between the results of the manual reference method and the automated sampler method. Further, a sampling apparatus and method is needed that can enable near real-time sampling and/or automated sampling under near reference manual method type equilibration conditions in order to obtain near real-time and/or automated results, which will enable even more consistently comparable particulate matter measurements than are available through the manual reference and existing automated apparatus and methods.

The existing apparatus and methods for measuring particulate matter suspended in a gaseous medium do not offer the flexibility and inventive features of the present sample gas stream conditioners, system and methods. As will be described in greater detail hereinafter, the features and advantages of the present invention differ from those previously proposed.

SUMMARY OF THE INVENTION

According to the present invention, there is provided a sample gas stream conditioner assembly for use with a particulate matter measuring instrument and a system and methods incorporating the same. The sample gas stream conditioner assembly comprises a sample gas stream conduit for receiving a sample gas stream and conducting the sample gas stream to the measuring instrument. A moisture exchanger and a humidity sensor are in communication with the conduit and a humidity control device is in gas flow relationship with the moisture exchanger. The moisture exchanger, humidity sensor and humidity control device serve to condition the sample gas stream, wherein the humidity level of the sample gas stream is regulated to obtain a selectable humidity level as the sample gas stream is conducted to a particulate matter collector of the measuring instrument.

Another feature of the invention relates to the preferred elements of a heat exchanger and a temperature sensor in communication with the conduit and a temperature control device in communication with the heat exchanger. These three elements serve to further condition the sample gas stream, wherein the temperature of the sample gas stream is regulated to obtain a selectable temperature as the sample gas stream is conducted to a particulate matter collector of the measuring instrument.

Still another feature of the invention concerns an ambient condition sensor system which can be integrated with the conditioner assembly to further assist in conditioning the sample gas stream.

Yet another feature of the invention is an automatic control unit wherein various components of the invention are automatically operated and in communication with one another to provide near real-time particulate matter measurements in the field, preferably under selectable constant humidity and temperature conditions.

This invention also contemplates a conditioning method in which a humidity level at a particulate matter collector in a particulate matter measurement instrument is regulated and various approaches for accomplishing this objective.

In accordance with the following, it is an advantage of the present invention to be able to collect particulate matter and maintain a sample gas stream at selectable humidity and/or temperature conditions, thereby bringing results between automated and manual reference methods and apparatus into closer agreement.

A further advantage is to maintain constant selectable humidity and temperature conditions to enhance apparatus and water mass stability thereby reducing both real and apparent mass changes in the particulate matter due to humidity changes or temperature effects.

Yet a further advantage is to be able to collect and measure particulate matter at lower temperatures without the undesired effects of humidity, thus also, reducing the loss of non-water volatiles that contribute to a more consistent particulate matter mass measurement.

DESCRIPTION OF THE DRAWINGS

Other features and advantages of the invention will become more readily apparent upon reference to the following description when taken in conjunction with the accompanying drawings, which drawings illustrate several embodiments of the invention.

DETAILED DESCRIPTION OF THE PREFERRED EMBODIMENTS

Figure 1:
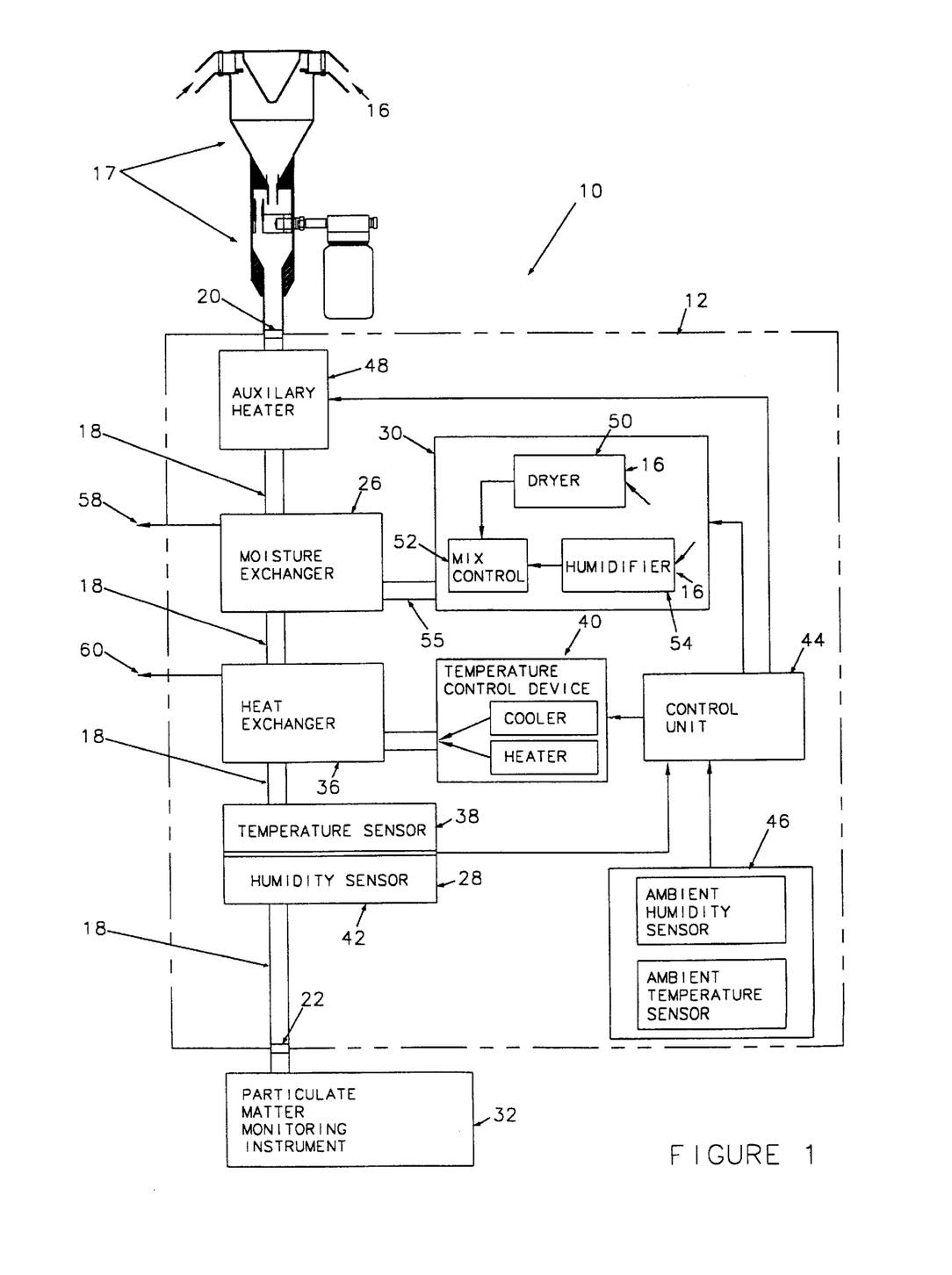
FIG. 1 is a schematic representation of several preferred embodiments of conditioner assemblies, a system and methods in accordance with the features of the present invention.

Referring now to the drawings, and particularly FIG. 1, there is depicted a schematic representation of a system 10 for measuring particulate matter in a sample gas stream. The system comprises a sample gas stream conduit 18 having a conduit inlet 20 and an outlet 22. Preceding the conduit inlet 20 is preferably located a conventional PM-10 or PM-2.5 particulate matter inlet device 17, which conforms to PM-10 or PM-2.5 standards for the collection of particulate matter in ambient air. A sample gas stream conditioner 12 is in communication with the sample gas stream conduit. A particulate matter measurement or monitoring instrument 32 is in communication with the sample gas stream outlet and serves to enable near real-time or automated measuring of particulate matter mass in the sample gas stream.

The measurement instrument 32 includes a collection media preferably a filter media, by which particulate matter is collected and measured. The filter media is preferably located near the outlet 22 to ensure that not only will the sample gas stream be conditioned to a selected humidity level and/or temperature, as described hereinafter, but also, the filter will be conditioned to essentially the same humidity level and/or temperature due to its proximity to the outlet. This invention may be implemented with several existing particulate matter measurement instruments that are associated with the prior manual reference or automated apparatus and methods, but it is preferred that the measurement instrument 32 comprise a TEOM® system as sold by Rupprecht & Patashnick Co., Inc., of Albany, N.Y., and particularly a Series 1400A TEOM® system.

The sample gas stream conditioner includes a moisture control system. The moisture control system regulates a humidity level of the sample gas stream flowing through the sample gas stream conduit to maintain a selectable humidity level as the sample gas stream flows out of the outlet 22. The moisture control system preferably comprises a moisture exchanger 26 and a humidity sensor 28, each in communication with the sample gas stream conduit, and, a humidity control device 30 in gas flow relationship with the moisture exchanger.

Figure 2:
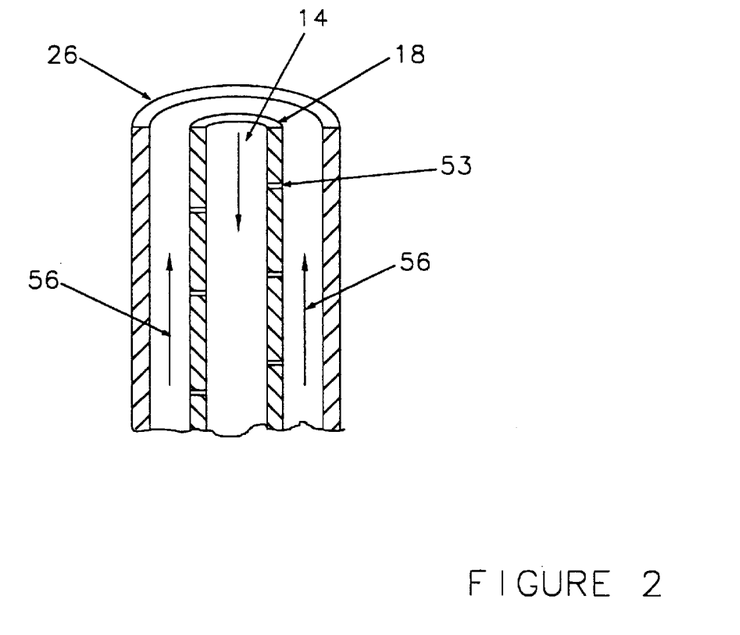
FIG. 2 is a cut away sectional view showing a portion of a sample gas stream conduit and a portion of a moisture exchanger in accordance with the features of the present invention.

As depicted in FIG. 2, in operation the sample gas stream preferably flows in a direction 14 opposite to that of a direction 56 for a purge gas (explained hereinafter). In the moisture exchanger portion of the conduit 18, the exchanger 26 is in moisture exchange communication with the conduit wherein water moisture can be added to or subtracted from the sample gas stream. Excellent results are obtained when the moisture exchanger comprises a Perma Pure PD™-Series gas dryer of a multi-tube Nafion® construction, as sold by Perma Pure Inc. of Toms River, N.J. The moisture control system further includes the humidity sensor 28. Preferably, the humidity sensor is located in or near the outlet of the conduit 18 and in communication therewith by conventional means. The sensor senses the humidity level of the sample gas stream and communicates this information to a control unit 44.

Returning to FIG. 1, the humidity control device may comprise a dryer 50 and a humidifier 54, each in gas flow relationship with a mixer control 52 such as a conventional solenoid operated valve. In this configuration, the dryer 50 may comprise a desiccant type dryer device such as a gas drying jar known as the model Hammond 26800 sold by Fisher Scientific of Pittsburgh, Pa. However, the dryer may comprise any conventional desiccant or thermoelectric cooler as a condenser, in order to dry the ambient air to provide a dry air supply. The humidifier 54 may comprise a Perma Pure MD™-Series Nafion® gas dryer, as sold by Perma Pure Inc. of Toms River, N.J., or any conventional device that can transfer water from a reservoir to a gaseous state to humidify the ambient air to provide a moist air supply. In operation, the dryer 50 and humidifier 54 take in ambient air 16 and produce dry and humid air, respectively, which is mixed as needed by the mixer control 52 and then supplied as a purge gas to the moisture exchanger through a common conduit 55. Also, depending on the moisture control components used, supplies of desiccant and moisture may be conserved by recirculating the purge gas at exhaust 58 through conventional means.

The sample gas stream conditioner further preferably includes a heat control system. The heat control system regulates a temperature of the sample gas stream flowing through the sample gas stream conduit to maintain a selectable temperature as the sample gas stream flows out of the sample gas stream conduit. The heat control system preferably comprises a heat exchanger 36 and a temperature sensor 38 in communication with the sample gas stream conduit, and, a temperature control device 40 in communication with the heat exchanger.

Figure 3:
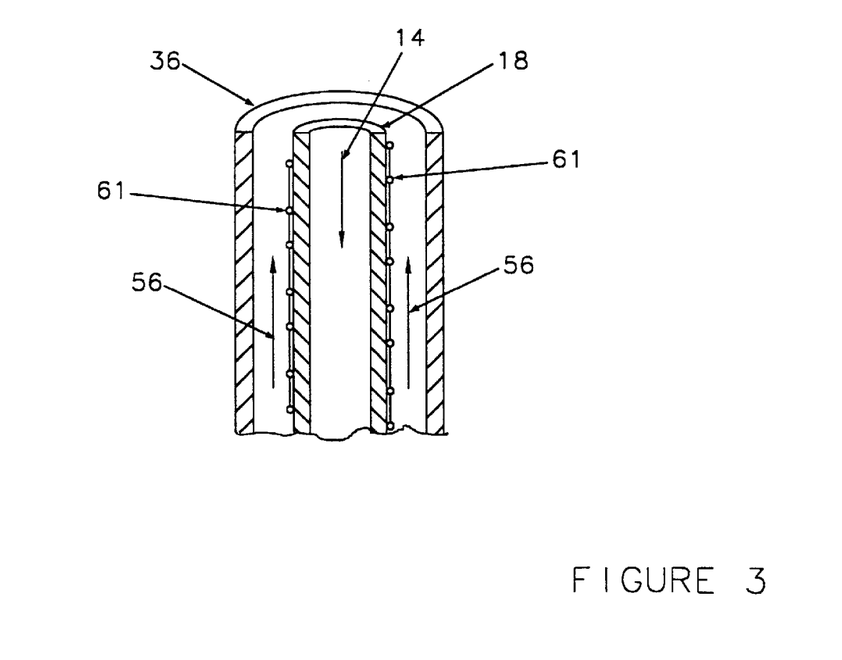
FIG. 3 is a cut away sectional view showing a portion of a sample gas stream conduit and a portion of a heat exchanger in accordance with the features of the present invention.

The heat control system preferably operates as depicted in FIG. 3. The heat exchanger is not in a moisture exchange relationship with the conduit 18 and no moisture is intended to pass into or out of the conduit 18 when the sample gas stream passes through the heat exchanger. It is desired, though, that the sample gas stream flow in a direction 14 opposite to that of a direction 56. The heat exchanger may comprise any conventional heat exchange member (e.g., a heated or cooled liquid or gas, a heating or cooling element, etc., as generally known in the art). Excellent results are obtained when the heat exchanger comprises a tube-in-tube arrangement as depicted and the inner tube or conduit portion 18 is stainless steel. The outer tube or portion 36 may comprise a PVC tube or any other material that enables the desired features here. The temperature control device preferably comprises a conventional heater 62 for operating conventional heating coils 61 which supply heat to the heat exchanger as needed. A cooler 64, such as a Vortex Cooler™ Enclosure Cooler, as sold by ITW Vortec, an Illinois Tool Works Company of Cincinnati, Ohio, is preferably included with the temperature control device for providing cool air in the direction 56, to cool the heat exchanger as needed. In this embodiment, the control unit 44 directly controls the cooler 64 and heater 62 and instructs them respectively, as needed, when to supply cool air or heat. However, other components may be used and other control arrangements may be employed, as know in the art, to achieve the heat exchange features of this invention. Depending on the temperature control device components(s), the heat exchanger may include a heat exchange exhaust 60 to recirculate cooling and/or heating substances through conventional means.

Analogous to the moisture control system, the heat control system further includes the temperature sensor 38. Preferably, the temperature sensor is located in or near the outlet of the conduit 18 and in communication therewith by conventional means. The sensor senses the temperature level of the sample gas stream and communicates this information to the control unit 44. Depending on the desired conditioner 12, the temperature sensor and/or the humidity sensor comprise the sensor system 42, which may be a single device or a combination of devices, as conventionally known in the art. For example, the humidity sensor for the sensor system 42 and the humidity feature of the ambient sensor system may comprise an ELAN HM2000-Series Relative Humidity Module as sold by Elan Technical Corporation of Fairfield, Conn. Further, the temperature sensor for the sensor system 42 and the temperature feature of the ambient sensor system may comprise a model AD592LN sold by Analog Devices of Norwood, Mass.

The conditioner 12 preferably also includes the control unit 44. This unit 44 is in communication with at least the humidity control device 30 and the humidity sensor 28 or sensor system 42, by conventional signal communication means. In this way, the control unit 44 monitors the sensor system and controls the humidity control device thereby regulating the humidity level of the sample gas stream to a selected humidity level. The control unit may provide for manual or automatic monitoring, controlling, and regulating of the conditioner and system, by conventional means. The control unit can comprise a conventional electronic control circuit or microprocessor control wherein the features of the present invention can be attained. The control unit may be independent of, interconnected to, or integrated with an overall controller of measuring instrument 32.

Depending on the desired conditioner 12, the control unit 44 may also be in communication with the temperature control device and the temperature sensor 38 or sensor system 42, by conventional signal communication means. In this way, the control unit 44 can also monitor the sensor system and control the temperature control device to thereby regulate the temperature of the sample gas stream to a selected temperature, either manually or automatically as previously discussed.

Conditioner 12 preferably also includes an ambient condition sensor system 46. The ambient condition sensor system is in communication with the control unit 44, by conventional signal communication means. In operation, the control unit monitors the ambient condition sensor system 46 and can use this information to assist it in regulating the humidity level and/or temperature of the sample gas stream to a selected humidity level and/or temperature. The ambient condition sensor system comprises a conventional sensor device(s) that monitors at least one condition of the ambient air, such as, humidity level and/or temperature, and then relays this information to the control unit. This feature may be manually or automatically operated.

Still another feature the conditioner preferably includes is an auxiliary heater 48. The heater 48 is in communication with the sample gas stream conduit to maintain the sample gas stream in a substantially gaseous state as the sample gas stream flows through the sample gas stream conduit, namely, as it passes through the moisture exchanger. For example, if the ambient conditions outside the conduit (as sensed, for example, by ambient condition sensor system 46 and monitored by control unit 44) are lower than the selected humidity level when adjusted to the selected temperature, thus requiring moisture to be added to the sample gas stream, the auxiliary heater 48 can be directed by control unit 44 to heat the sample gas stream some (but preferably not to exceed the selected temperature) before moisture is added to prevent the possibility of condensation. Further, in certain situations, it may be desirable for the moisture exchanger itself to be separately cooled or heated (by conventional means) to prevent a condensation problem or undesired evaporation of moisture from the purge gas. As such, this feature is included within the scope of the present invention.

Other features of this invention comprise a method for measuring particulate matter suspended in the sample gas stream. As a first step, ambient air 16 enters the conduit 18, after passing through inlet device 17, and is received as the sample gas stream at the conduit inlet 20. The stream preferably flows in the downward direction 14 through the conduit while being conducted to the particulate matter measuring instrument.

The conduit 18 is preferably a straight tube enabling easy flow therethrough in order to reduce turbulence or particle losses. The conduit is constructed by conventional means in accordance with the features of this invention. In particular, excellent results are achieved when the conduit comprises a continuous path that is constructed of stainless steel whereby the conduit is essentially impermeable along its length from the conduit inlet 20 to the outlet 22, except for the portion of the conduit extending through the moisture exchanger where it is permeable to water and impermeable to all fluids or gases except water.

Next, the humidity level of the sample gas stream is regulated to maintain the selected humidity level of the sample gas stream and thereby provide a humidity regulated sample gas stream. In particular, the humidity level of the sample gas stream is sensed by sensor 28 to obtain a humidity level sensed result. This result is communicated to the control unit 44. The control unit interprets the humidity level sensed result to obtain a humidity level interpretation. Based on the humidity level interpretation, the control unit communicates with the humidity control device 30 instructing it to increase or decrease the humidity level of the moisture exchanger. The humidity level of the purge gas is mixed as needed and then circulated within the moisture exchanger 26 and through moisture exchange relationship with the conduit and by the laws of thermodynamics the humidity level of the sample gas stream is adjusted, thereby regulating the humidity level of the sample gas stream to maintain the selected humidity level.

Next, though practically it occurs near simultaneously, the temperature of the sample gas stream is regulated to maintain the selected temperature of the sample gas stream and thereby provide a temperature regulated sample gas stream. In particular, the temperature of the sample gas stream is sensed by sensor 38 to obtain a temperature sensed result. This result is communicated to the control unit 44. The control unit interprets the temperature sensed result to obtain a temperature interpretation. Based on the temperature interpretation, the control unit communicates with the temperature control device 40 instructing it to increase or decrease the temperature of the heat exchanger. The heat control device component(s) increases or decreases the temperature in the heat exchanger proximate the conduit and by the laws of thermodynamics the temperature of the sample gas stream is adjusted, thereby regulating the temperature of the sample gas stream to maintain the selected temperature.

The conditioner 12 may include humidity level sensing and/or temperature sensing of the sample gas stream, although preferably it includes both. In such a case, then the method includes sensing and interpreting steps that are integrated. That is, the control unit will integrate the humidity level interpretation and the temperature interpretation to obtain a first integrated interpretation. Such integrating is often desirable because of the relationship between temperature and the humidity level or relative humidity. In particular, relative humidity is defined as the amount of moisture in the air as compared with the maximum amount that the air could contain at the same temperature, expressed as a percentage. Therefore, for obvious reasons to one of ordinary skill in the art, considering both humidity level and temperature may be desired when attempting to regulate one or both of them. Based on the first integrated interpretation, the control unit communicates with the temperature control device and the humidity control device instructing each, as necessary, to increase or decrease the humidity level of the purge gas and/or temperature of the heat exchange member, respectively. Accordingly, the humidity level and the temperature of the sample gas stream are regulated to maintain the selected humidity level and temperature.

Next, though practically it occurs simultaneously, the method may include monitoring an ambient condition through the ambient condition sensor system 46. In particular, the humidity level and/or temperature of the ambient air is monitored by sensor system 46 and this information is communicated to the control unit 44. The control unit interprets the ambient condition to obtain an ambient condition interpretation. The control unit then integrates the ambient condition interpretation with the humidity level interpretation, the temperature interpretation, or both, to obtain a humidity level integrated interpretation, a temperature integrated interpretation or a second integrated interpretation, respectively. The integration here is again desirable for reasons analogous to those previously discussed. Based on the integrated interpretation, the control unit communicates with the temperature control device and the humidity control device instructing each, as necessary, to increase or decrease the humidity level of the moisture exchanger and/or temperature of the heat exchanger, respectively. Accordingly, the humidity level and/or the temperature of the sample gas stream can be regulated to maintain the selected humidity level and/or temperature in view of the sensed gas stream and ambient conditions. As earlier described, the sensed ambient conditions may also be used to control operation of auxiliary heater 48, e.g., in order to avoid condensation within conduit 18.

Finally, the last step comprises measuring the particulate matter suspended in the humidity and/or temperature regulated sample gas stream. Preferably, the measuring is performed with a near real-time automated sampler as discussed hereinabove. In this regard, it is preferred that the conduit 18 be as short as possible to reduce the time between entrance of the sample gas stream into the conduit and its exit out of the outlet, yet long enough to include the desired features of the invention. The mass of particulate matter in the sample gas stream is measured once particulate matter is collected by the filter media or other particulate matter collector.

For both the method and conditioner of this invention, the selectable humidity level is preferably selected in the range of 20% to 45% ±5% relative humidity and the selectable temperature is preferably selected in the range of 15° C. to 30° C. ±3° C. in order to match the equilibrium conditions of the manual reference method. However, it should be understood that other humidity levels and temperatures could be selected and the features and advantages of the present invention would still be attained. For the present application of this invention it is preferred to maintain a substantially constant selected humidity level and/or temperature, although other controlled humidity levels and temperatures may be provided by the present invention.

The present invention may be practiced in a continuously operating state or it may be intermittently operated. It is presently contemplated to be preferably operated in a continuous state wherein sampling, conditioning and measuring of the particulate matter in the sample gas stream occurs continuously. However, it is within the scope of the present invention as claimed to include intermittent sampling and/or conditioning and/or measuring of particulate matter. For example, such an application could comprise sampling a sample gas stream for twenty-three hours without conditioning the sample gas stream or measuring particulate matter in the sample gas stream. Then, between hours twenty-three and twenty-four, the conditioner could be operated and the sample gas stream utilized to bring the previously collected particulate matter and newly collected particulate matter, and the particulate matter collector, to within selectable humidity level and temperature conditions. Measuring could then be conducted just between hours twenty-three and twenty-four, or at the end of hour twenty-four. The conditioning and/or measuring may then be discontinued for a like period and resumed for a like period. It is understood that any time period(s) could be employed and that the time period discussed above is only an example of the possible applications of this invention.

This invention also comprises a method for conditioning a particulate matter collector and particulate matter. A first step comprises locating the particulate matter collector (not specifically shown in the drawings, but which is a conventional component in a particulate matter measurement instrument 32) in the particulate matter measurement instrument. Preferably, the instrument is located in the field so that conditioning of the collector and/or particulate matter can be conducted in the field.

The particulate matter collector is then conditioned. As previously discussed, conditioning includes regulating a humidity level to maintain a selectable humidity level at the particulate matter collector. The conditioning may be accomplished, for example, using the apparatus disclosed in FIG. 1 and as described above. However, the conditioning could be accomplished using other means, such as a closed-environment type mode in which an environment surrounding the particulate matter collector, and thus in effect the collector itself, is conditioned to the selectable humidity level using appropriate means, such as for example, the moisture control system, to regulate a humidity level of the static enclosed environment.

This method also preferably comprises a second step, although practically it occurs simultaneously, of conditioning the particulate matter collector to regulate a temperature of the collector to a selectable temperature. This temperature conditioning may be accomplished analogous to that for humidity level conditioning. At this point in this method the particulate matter collector has essentially been equilibrated, preferably to conditions comparable to the manual reference method, and the mass of the collector can be measured to provide a base line against which to compare the collector as it collects particulate matter during sampling.

Next, this method preferably includes receiving a sample gas stream and conducting the sample gas stream to the particulate matter collector where particulate matter suspended in the sample gas stream is collected by the particulate matter collector. Then the particulate matter is preferably conditioned by regulating a humidity level of the particulate matter and/or collected particulate matter. In particular, the humidity level of the particulate matter and the particulate matter collector will be the same at this point and together they can be conditioned to the same selectable humidity level.

This step will also preferably include conditioning the temperature of the particulate matter and/or the collected particulate matter to the selectable temperature for the particulate matter and the particulate matter collector alike. The humidity level and/or temperature conditioning for the particulate matter and the particulate matter collector can be accomplished analogously to that for the particulate matter collector alone. At this point in this method, the particulate matter collector and the collected particulate matter has been essentially equilibrated, preferably to conditions comparable to the manual reference method, and the collected mass can be measured to provide a collected particulate matter mass measurement. As discussed herein, the receiving or sampling, conditioning, and measuring may be conducted one or more times and on an intermittent or continuous basis.

Another feature this method may include is flowing a substantially particle-free stream of gas into communication with the particulate matter collector and/or the collected particulate matter for conditioning the same. In this way sampling may be conducted for a certain time and then the sampling conduit closed by appropriate means. Next, the stream of gas, preferably particle-free or substantially particle-free, is communicated to and with the particulate matter collector and/or collected particulate matter. For example, using the apparatus in FIG. 1, and as described above, a humidity level and/or temperature conditioned sample gas stream could be provided in the conduit 18 wherein the sample gas stream passes through a conventional pre-filter media (not specifically shown) to substantially eliminate any particles or particulate matter therein and thus comprise a substantially particle-free stream of humidity level and temperature conditioned gas. This stream of gas can then be communicated to the particulate matter collector and/or collected particulate matter to maintain the selectable humidity level and/or temperature of the same.

In addition to the above-described embodiments of the invention, another embodiment comprises a sample gas stream conditioner assembly for use with particulate matter measuring instrument wherein the sample gas stream conditioner includes a heat control system that regulates a temperature of a sample gas stream or gas stream to maintain a selectable temperature less than 30° C. at least proximate a particulate matter collector. Further, the conditioner includes, for example, a moisture exchanger and dryer, or conventional device(s), for reducing a humidity level of the sample gas stream without regulating the humidity level.

Analogous to the embodiment depicted in FIG. 1 and described hereinabove, this conditioner assembly may include the sample gas stream conduit 18 having the inlet 20 and outlet 22. The sample gas stream conditioner is in communication with the sample gas stream conduit. The heat control system preferably includes, for example, the temperature control device 40 and the temperature sensor 38, and the control unit 44. These elements operate as previously described in detail. However, here the heat control system regulates the temperature of the sample gas stream to maintain the selectable temperature which is less than 30° C. It is preferred not to exceed 30° C. to avoid undesired evaporation of ammonium nitrite particulate matter, which evaporation occurs at temperatures exceeding 30° C., as well as other possible undesired evaporation of other particulate matter.

A further feature of this embodiment comprises, for example, a moisture exchanger 26 and a dryer 50. In operation the dryer operates continuously, as desired, to supply a dry purge gas to the moisture exchanger. The moisture exchanger serves to uncontrollably reduce the humidity level of a sample gas stream therein. Accordingly, the sample gas stream is only temperature regulated, but the undesired effects of humidity level variations in the field are substantially reduced. That is, since the humidity level, and thus the effects of a variable humidity level, are reduced without the use of high temperatures, the more volatile particulate matter components that would be lost through a higher temperature control method are conserved. Thus, this embodiment enables more comparable particulate matter measurements when sampling and measuring particulate matter suspended in a sample gas stream by regulating only temperature.

As there are various possible embodiments of the invention and various changes that might be made in the embodiments above set forth, it is understood that all of the above matters here set forth or shown in the accompanying drawings are to be interpreted as illustrative and not in a limiting sense.

What is claimed is:

1. A sample gas stream conditioner assembly for use with a particulate matter mass measuring instrument having a particulate matter collector, the sample gas stream conditioner assembly comprising:

first means for receiving a sample gas stream and conducting the sample gas stream to the collector of the measuring instrument; and second means for conditioning the sample gas stream, wherein the second means regulates the humidity level of the sample gas stream to obtain a selectable humidity level in the range of 20% to 40%, ±5% relative humidity at least proximate the collector of the measuring instrument and regulates a temperature of the sample gas stream to obtain a selectable temperature at least proximate the collector of the measuring instrument.

2. The sample gas stream conditioner assembly of claim 1, wherein the second means comprises a heat exchanger and a temperature sensor in communication with the first means and a temperature control device in communication with the heat exchanger.

3. The sample gas stream conditioner assembly of claim 1, in combination with a particulate matter mass measuring instrument, the measuring instrument being in communication with the first means and enabling real-time sampling and measuring of the sample gas stream.

4. The sample gas stream conditioner assembly of claim 1, wherein the second means further maintains the sample gas stream in a substantially gaseous state as the sample gas stream is conducted by the first means.

5. The sample gas stream conditioner assembly of claim 2, wherein the second means regulates the humidity level and the temperature to obtain a constant selectable humidity level and temperature.

6. The sample gas stream conditioner assembly of claim 1, wherein the sample gas stream conditioner assembly further comprises third means for automatically operating the second means.

7. The sample gas stream conditioner assembly of claim 1, wherein the second means regulates the humidity level to obtain a constant selectable humidity level.

8. The sample gas stream conditioner assembly of claim 1, wherein the first means comprises a straight conduit.

9. A system for measuring mass of particulate matter in a sample gas stream comprising:

a sample gas stream conduit having an inlet and an outlet;

a sample gas stream conditioner in communication with the sample gas stream conduit;

the sample gas stream conditioner including a moisture control system, wherein the moisture control system regulates a humidity level of the sample gas stream flowing through the sample gas stream conduit to maintain a selectable humidity level in the range of 20% to 45%, ±5% relative humidity at least proximate the outlet of the sample gas stream conduit and a heat control system, wherein the heat control system regulates a temperature of the sample gas stream flowing through the sample gas stream conduit to maintain a selectable temperature at least proximate the sample gas stream conduit outlet; and a particulate matter mass measurement instrument in communication with the sample gas stream conduit outlet.

10. The system of claim 9, further comprising a sensor system in communication with the sample gas stream conduit which senses at least one member from the group consisting of humidity level and temperature of the sample gas stream.

11. The system of claim 10, further comprising a control unit in communication with the moisture control system, the heat control system and the sensor system and wherein the control unit automatically monitors the sensor system and automatically controls the moisture control system and the heat control system.

12. The system of claim 11, further comprising an ambient condition sensor system in communication with the control unit and wherein the control unit automatically monitors the ambient condition sensor system.

13. The system of claim 9, wherein the particulate matter mass measurement instrument enables real-time measuring of particulate matter mass in the sample gas stream.

14. The system of claim 9, further comprising an auxiliary heater in communication with the sample gas stream conduit to maintain the sample gas stream in a substantially gaseous state as the sample gas stream flows through the sample gas stream conduit.

15. A system for measuring mass of particulate matter in a sample gas stream comprising:

a sample gas stream conduit having an inlet and an outlet;

a sample gas stream conditioner in communication with the sample gas stream conduit;

the sample gas stream conditioner including: a moisture control system, wherein the moisture control system regulates a humidity level of the sample aas stream flowing through the sample gas stream conduit to maintain a selectable humidity level at least proximate the outlet of the sample gas stream conduit, and a heat control system, wherein the heat control system regulates a temperature of the sample gas stream flowing through the sample gas stream conduit to maintain a selectable temperature at least proximate the sample gas stream conduit outlet;

a sensor system in communication with the sample gas stream conduit which senses the humidity level of the sample gas stream; and a particulate matter mass measurement instrument in communication with the sample gas stream conduit outlet.

16. The system of claim 15, further comprising a control unit in communication with the moisture control system and the sensor system and wherein the control unit automatically monitors the sensor system and automatically controls the moisture control system.

17. The system of claim 16, further comprising an ambient condition sensor system in communication with the control unit and wherein the control unit automatically monitors the ambient condition sensor system.

18. A method for measuring mass of particulate matter suspended in a sample gas stream, comprising;

receiving the sample gas stream in a sample gas stream conduit and conducting the sample gas stream to a particulate matter mass measuring instrument;

regulating a temperature of the sample gas stream to maintain a selectable temperature of the sample gas stream;

regulating a humidity level of the sample gas stream to maintain a selectable humidity level in the range of 20% to 45%, ±5% relative humidity of the sample gas stream at the particulate matter measuring instrument; and measuring mass of the particulate matter suspended in the sample gas stream.

19. The method of claim 18, further comprising sensing the temperature of the sample gas stream to obtain a temperature sensed result, interpreting the temperature sensed result to obtain a temperature interpretation and regulating the temperature of the sample gas stream based on the temperature interpretation.

20. The method of claim 19, wherein the steps of sensing, interpreting and regulating are controlled automatically by a control unit.

21. The method of claim 18, wherein the step of regulating includes regulating the humidity level and temperature to obtain a constant selectable humidity level and temperature.

22. The method of claim 18, wherein the step of regulating includes regulating the humidity level to obtain a constant selectable humidity level.

23. A method for measuring mass of particulate matter suspended in a sample gas stream, comprising;
   receiving the sample gas stream in a sample gas stream conduit and conducting the sample gas stream to a particulate matter mass measuring instrument;
   regulating a humidity level of the sample gas stream to maintain a selectable humidity level of the sample gas stream at the particulate matter measuring instrument, and regulating a temperature of the sample gas stream to maintain a selectable temperature of the sample gas stream;
   sensing the humidity level of the sample gas stream to obtain a humidity level sensed result, interpreting the humidity level sensed result to obtain a humidity level interpretation and regulating the humidity level of the sample gas stream based on the humidity level interpretation; and
   measuring mass of the particulate matter suspended in the sample gas stream.

24. The method of claim 23, wherein the steps of sensing, interpreting and regulating are controlled automatically by a control unit.

25. The method of claim 24, further comprising monitoring an ambient condition, interpreting the ambient condition to obtain an ambient condition interpretation and integrating the ambient condition interpretation and the humidity level interpretation to obtain a humidity level integrated interpretation wherein regulating the humidity level of the sample gas stream is based on the integrated interpretation.

26. A method for conditioning a particulate matter collector, comprising:
   locating the particulate matter collector in a particulate matter measurement instrument; and
   regulating a humidity level at the particulate matter collector in the instrument to maintain a selectable humidity level in the range of 20% to 45%, ±5% relative humidity at the particulate matter collector, and regulating a temperature at the particulate matter collector to maintain a selectable temperature at the particulate matter collector.

27. The method of claim 26, further comprising:
   receiving a sample gas stream;
   conducting the sample gas stream to the particulate matter collector wherein particulate matter in the sample gas stream is collected by the particulate matter collector thereby comprising collected particulate matter; and,
   wherein the step of regulating further includes regulating a humidity level and a temperature of the collected particulate matter to maintain a selectable humidity level and temperature of the collected particulate matter.

28. The method of claim 27, wherein the step of regulating includes flowing a substantially particle-free stream of gas into communication with the particulate matter collector and the collected particulate matter to maintain the selectable humidity level and temperature at the particulate matter collector and of the collected particulate matter.

29. The method of claim 26, further comprising:
   receiving a sample gas stream;
   conducting the sample gas stream to the particulate matter collector; and,
   wherein the step of regulating further includes regulating a humidity level of the particulate matter to maintain a selectable humidity level of the particulate matter.

30. The method of claim 29, wherein particulate matter in the sample gas stream is collected by the particulate matter collector thereby comprising collected particulate matter and wherein the step of regulating further includes regulating a humidity level of the collected particulate matter to maintain a selectable humidity level of the collected particulate matter.

31. The method of claim 30, wherein the step of regulating includes flowing a substantially particle-free stream of gas into communication with the particulate matter collector and the collected particulate matter to maintain the selectable humidity level at the particulate matter collector and of the collected particulate matter.

32. A sample gas stream conditioner assembly for use with a particulate matter mass measuring instrument having a particulate matter collector, the sample gas stream conditioner assembly comprising:
   first means for receiving a sample gas stream and conducting the sample gas stream to the collector of the measuring instrument;
   second means for conditioning the sample gas stream, wherein the second means regulates the humidity level of the sample gas stream to obtain a selectable humidity level at least proximate the collector of the measuring instrument; and
   third means for automatically operating the second means, wherein the third means further monitors an ambient condition and interprets the ambient condition to assist the second means in conditioning the sample gas stream and wherein the ambient condition comprises humidity.

33. A method for measuring mass of particulate matter suspended in a sample gas stream, comprising:
   receiving the sample gas stream in a sample gas stream conduit and conducting the sample gas stream to a particulate matter mass measuring instrument;
   regulating a humidity level of the sample gas stream to maintain a selectable humidity level of the sample gas stream at the particulate matter measuring instrument;
   regulating a temperature of the sample gas stream to maintain a selectable temperature of the sample gas stream;
   sensing the temperature of the sample gas stream to obtain a temperature sensed result, interpreting the temperature sensed result to obtain a temperature interpretation and regulating the temperature of the sample gas stream based on the temperature interpretation;
   sensing the humidity level of the sample gas stream to obtain a humidity level sensed result, interpreting the humidity level sensed result to obtain a humidity level interpretation, integrating the humidity level interpretation and the temperature interpretation to obtain a first integrated interpretation and regulating the humidity level and the temperature of the sample gas stream based on the first integrated interpretation; and measuring mass of the particulate manner suspended in the sample gas stream.

34. A sample gas stream conditioner assembly for use with a particulate matter mass measuring instrument having a particulate matter collector, the sample gas stream conditioner assembly comprising:

first means for receiving a sample gas stream and conducting the sample gas stream to the collector of the measuring instrument;

second means for conditioning the sample gas stream, wherein the second means regulates the humidity level and temperature of the sample gas stream to obtain a selectable humidity level and a selectable temperature at least proximate the collector of the measuring instrument, and wherein the second means comprises a moisture exchanger and a humidity sensor in communication with the first means and a humidity control device in gas flow relationship with the moisture exchanger.

35. A sample gas stream conditioner assembly for use with a particulate matter matter measuring instrument having a particulate matter collector, the sample gas stream conditioner assembly comprising:

first means for receiving a sample gas stream and conducting the sample gas stream to the collector of the measuring instrument;

second means for conditioning the sample gas stream, wherein the second means regulates the humidity level of the sample gas stream to obtain a selectable humidity level at least proximate the collector of the measuring instrument and regulates a temperature of the sample gas stream to obtain a selectable temperature at least proximate the collector of the measuring instrument, and wherein the second means comprises a heat exchanger and a temperature sensor in communication with the first means and a temperature control device in communication with the heat exchanger, and wherein the second means further comprises a moisture exchanger and a humidity sensor in communication with the first means and a humidity control device in gas flow relationship with the moisture exchanger.

36. The sample gas stream conditioner assembly of claim 35, wherein the second means further includes an auxiliary heater upstream of the moisture exchanger.

37. A sample gas stream conditioner assembly for use with a particulate matter mass measuring instrument having a particulate matter collector, the sample gas stream conditioner assembly comprising:

first means for receiving a sample gas stream and conducting the sample gas stream to the collector of the measuring instrument; and second means for conditioning the sample gas stream, wherein the second means regulates the humidity level of the sample gas stream to obtain a selectable humidity level in the range of 20% to 40%, ±5% relative humidity at least proximate the collector of the measuring instrument, and maintains the sample gas stream in a substantially gaseous state as the sample gas stream is conducted by the first mean.

38. A sample gas stream conditioner assembly for use with a particulate matter mass measuring instrument having a particulate matter collector, the sample gas stream conditioner assembly comprising:

first means for receiving a sample gas stream and conducting the sample gas stream to the collector of the measuring instrument; and second means for conditioning the sample gas stream, wherein the second means regulates the humidity level of the sample gas stream to obtain a selectable humidity level at least proximate the collector of the measuring instrument, and regulates a temperature of the sample gas stream to obtain a selectable temperature at least proximate the collector of the measuring instrument and, wherein the selectable humidity level is in the range of 20% to 45%, ±5% relative humidity and the selectable temperature is in the range of 15° C. to 30° C., ±° C.

39. A system for measuring mass of particulate matter in a sample gas stream comprising:

a sample gas stream conduit having an inlet and an outlet;

a sample gas stream conditioner in communication with the sample gas stream conduit;

the sample gas stream conditioner including a heat control system, wherein the heat control system regulates a temperature of the sample gas stream flowing through the sample gas stream conduit to maintain a selectable temperature at least proximate the sample gas stream conduit outlet;

the sample gas stream conditioner including a moisture control system, wherein the moisture control system regulates a humidity level of the sample gas stream flowing through the sample gas stream conduit to maintain a selectable humidity level at least proximate the outlet of the sample gas stream conduit, and wherein the moisture control system comprises a moisture exchanger and a humidity sensor in communication with the sample gas stream conduit and a humidity control device in gas flow relationship with the moisture exchanger; and a particulate matter mass measurement instrument in communication with the sample gas stream conduit outlet.

40. A system for measuring mass particulate matter in a sample gas stream comprising:

a sample gas stream conduit having an inlet and an outlet;

a sample gas stream conditioner in communication with the sample gas stream conduit;

the sample gas stream conditioner including a moisture control system, wherein the moisture control system regulates a humidity level of the sample gas stream flowing through the sample gas stream conduit to maintain a selectable humidity level at least proximate the outlet of the sample gas stream conduit;

a heat control system which regulates a temperature of the sample gas stream flowing through the sample gas stream conduit to maintain a selectable temperature at least proximate the sample gas stream conduit outlet, and wherein the heat control system comprises a heat exchanger and a temperature sensor in communication with the sample gas stream conduit and a temperature control device in communication with the heat exchanger; and a particulate matter measurement instrument in communication with the sample gas stream conduit outlet.

41. A system for measuring mass of particulate matter in a sample gas stream comprising:

a sample gas stream conduit having an inlet and an outlet;

a sample gas stream conditioner in communication with the sample gas stream conduit;

the sample gas stream conditioner including a moisture control system, wherein the moisture control system regulates a humidity level of the sample gas stream flowing through the sample gas stream conduit to maintain a selectable humidity level in the range of 20% to 45%, ±5% relative humidity at least proximate the outlet of the sample gas stream conduit;

a heat control system which regulates a temperature of the sample gas stream flowing through the sample gas stream conduit to maintain a selectable temperature in the range of 15° C. to 30° C., ±3° C. at least proximate the sample gas stream conduit outlet; and a particulate matter mass measurement instrument in communication with the sample gas stream conduit outlet.

42. The method of claim 33, wherein the steps of sensing, interpreting and regulating are controlled automatically by a control unit.

43. The method of claim 42, further comprising monitoring an ambient condition, interpreting the ambient condition to obtain an ambient condition interpretation and integrating the ambient condition interpretation and the temperature interpretation and the humidity level interpretation to obtain a second integrated interpretation wherein regulating the humidity level and the temperature of the sample gas stream is based on the second integrated interpretation.

44. A method for measuring mass of particulate matter suspended in a sample gas stream, comprising:

receiving the sample gas stream in a sample gas stream conduit and conducting the sample gas stream to a particulate matter mass measuring instrument;

regulating a humidity level of the sample gas stream to maintain a selectable humidity level of the sample gas stream at the particulate matter mass measuring instrument;

regulating a temperature of the sample gas stream to maintain a selectable temperature of the sample gas stream;

sensing the temperature of the sample gas stream to obtain a temperature sensed result, interpreting the temperature sensed result to obtain a temperature interpretation and regulating the temperature of the sample gas stream based on the temperature interpretation;

wherein the steps of sensing, interpreting and regulating are controlled automatically by a control unit;

monitoring an ambient condition, interpreting the ambient condition to obtain an ambient condition interpretation and integrating the ambient condition interpretation and the temperature interpretation to obtain a temperature integrated interpretation wherein regulating the temperature of the sample gas stream is based on the integrated interpretation; and measuring mass of the particulate matter suspended in the sample gas stream.

45. A method for measuring mass of particulate matter suspended in a sample gas stream, comprising:

receiving the sample gas stream in a sample gas stream conduit and conducting the sample gas stream to a particulate matter mass measuring instrument;

regulating a humidity level of the sample gas stream to maintain a selectable humidity level of the sample gas stream at the particulate matter mass measuring instrument;

regulating a temperature of the sample gas stream to maintain a selectable temperature of the sample gas stream; and wherein the selectable humidity level is in the range of 20% to 45%, ±5% relative humidity and the selectable temperature is in the range of 5° C. to 30° C., ±3° C.

46. A sample gas stream conditioner assembly for use with a particulate matter mass measuring instrument having a particulate matter collector, the sample gas stream conditioner assembly comprising:

first means for receiving a sample gas stream and conducting the sample gas stream to the collector of the measuring instrument;

second means for conditioning the sample gas stream, wherein the second means regulates the humidity level of the sample gas stream to obtain a selectable humidity level at least proximate the collector of the measuring instrument, and regulates a temperature of the sample gas stream to obtain a selectable temperature at least proximate the collector of the measuring instrument; and third means for automatically operating the second means, wherein the third means further monitors an ambient condition and interprets the ambient condition to assist the second means in conditioning the sample gas stream and wherein the ambient condition comprises a member from the group consisting of humidity and temperature.

47. The sample gas stream conditioner assembly of claim 46, wherein the ambient condition comprises both humidity and temperature.

* * * * *

UNITED STATES PATENT AND TRADEMARK OFFICE
CERTIFICATE OF CORRECTION

PATENT NO. : 6,151,953
DATED : November 28, 2000
INVENTOR(S) : Patashnick et al.

It is certified that error appears in the above-identified patent and that said Letters Patent is hereby corrected as shown below:

Claim 15, column 12,
Line 30, delete "aas" and replace with -- gas --.

Claim 38, column 16,
Line 16, delete ",±°C" and replace with -- ± 3° C --.

Signed and Sealed this

Twenty-fifth Day of September, 2001

Attest:

NICHOLAS P. GODICI
Attesting Officer
Acting Director of the United States Patent and Trademark Office